United States Patent
Kitching et al.

(10) Patent No.: US 8,044,954 B2
(45) Date of Patent: Oct. 25, 2011

(54) SYSTEM AND METHOD FOR AUTOMATIC CONSTRUCTION OF TOOTH AXES

(75) Inventors: Ian Kitching, Saratoga, CA (US);
Roman Roschin, Moscow (RU);
Fuming Wu, Pleasanton, CA (US);
Vadim Matov, San Jose, CA (US);
Alexey Vishnevskiy, Moscow (RU)

(73) Assignee: Align Technology, Inc., San Jose, CA (US)

(*) Notice: Subject to any disclaimer, the term of this patent is extended or adjusted under 35 U.S.C. 154(b) by 1139 days.

(21) Appl. No.: 11/776,466

(22) Filed: Jul. 11, 2007

(65) Prior Publication Data

US 2008/0076086 A1     Mar. 27, 2008

Related U.S. Application Data

(60) Provisional application No. 60/826,714, filed on Sep. 22, 2006.

(51) Int. Cl.
*G06T 17/00*     (2006.01)
*A61C 5/00*      (2006.01)

(52) U.S. Cl. .................................. 345/420; 433/215

(58) Field of Classification Search .................. None
See application file for complete search history.

(56) References Cited

U.S. PATENT DOCUMENTS

| | | | |
|---|---|---|---|
| 4,668,192 A * | 5/1987 | Lavin | 433/205 |
| 5,586,881 A | 12/1996 | Chikami | |
| 5,605,459 A | 2/1997 | Kuroda | |
| 5,975,893 A | 11/1999 | Chishti et al. | |
| 6,409,504 B1 | 6/2002 | Jones | |
| 6,471,511 B1 | 10/2002 | Chishti et al. | |
| 6,514,074 B1 | 2/2003 | Chishti et al. | |
| 6,767,208 B2 | 7/2004 | Kaza | |
| 7,063,532 B1 | 6/2006 | Jones et al. | |
| 2003/0039389 A1 | 2/2003 | Jones et al. | |
| 2004/0054304 A1 * | 3/2004 | Raby | 600/590 |
| 2006/0147872 A1 | 7/2006 | Andreiko | |

FOREIGN PATENT DOCUMENTS

| | | |
|---|---|---|
| EP | 0696444 | 2/1996 |
| WO | WO 99/58077 | 11/1999 |

* cited by examiner

*Primary Examiner* — Kee M Tung
*Assistant Examiner* — Carlos Perromat
(74) *Attorney, Agent, or Firm* — Brooks, Cameron & Huebsch, PLLC

(57) ABSTRACT

System and method for automatic construction of the tooth's axes in terms of three orthogonal unit vectors are disclosed. Three dimensional data for a tooth is used to automatically construct the tooth's axes. System and methods for automatic construction of the axes for different types of teeth such as incisors, canines, premolars, and molars are disclosed.

11 Claims, 18 Drawing Sheets

SYSTEM AND METHOD FOR AUTOMATIC CONSTRUCTION OF TOOTH AXES

CROSS-REFERENCE TO RELATED APPLICATIONS

This application claims priority to and benefit of U.S. Provisional Application No. 60/826,714, entitled "System and Method for Automatic Construction of Tooth Axes" and filed on Sep. 22, 2006.

FIELD OF INVENTION

The present invention relates generally to the field of orthodontics, and in particular to system and method for automatic construction of the tooth's axes in terms of three orthogonal unit vectors.

BACKGROUND OF THE INVENTION

One objective of orthodontics is to move a patient's teeth to positions where the teeth function optimally and are also aesthetically pleasing. Conventional appliances such as braces and wires are applied to the teeth of a patient by an orthodontist. Once mounted on the teeth, the braces exert continual force on the teeth and gradually urge the teeth to their respective ideal position. The orthodontist does this by adjusting the wires over time to move the teeth toward their final destination.

Orthodontic brackets are often bonded directly to the patient's teeth. Typically, a small quantity of adhesive is placed on the base of each bracket and the bracket is then placed on a selected tooth. Before the adhesive is set, the bracket is maneuvered to a desired location on the tooth. Once the adhesive has hardened, the bracket is bonded to the tooth with sufficient strength to withstand subsequent orthodontic forces as treatment progresses. One shortcoming with this technique is the difficulty in accessing the optimal surface for bracket placement on severely crowded teeth or in teeth where the bonding surface is obstructed by teeth in the opposing arch during jaw closure. With posterior teeth, the treatment provider may have difficulty seeing the precise position of the bracket relative to the tooth surface. The amount of time needed to carry out the bonding procedure may be a nuisance both to the patient as well as to the treatment provider. Also, the necessity of minimizing moisture contamination from the patient's saliva can prolong the procedure and also unduly impair the accuracy of placement of the brackets on the teeth. All of these factors increase the chance that one or more brackets will be incorrectly positioned on the teeth.

Apparatus, systems, and methods have been developed to facilitate teeth movement utilizing clear, removable teeth aligners as an alternative to braces. A system that utilizes multiple, removable aligners is described in U.S. Pat. No. 5,975,893, assigned to the same assignee as this application. A mold of the patient's bite is initially taken and desired ending positions for the patient's teeth (i.e., a functionally and/or aesthetically optimum position) are determined, based on a prescription provided by an orthodontist or dentist. Corrective paths between the initial positions of the teeth and their desired ending positions are then planned. These corrective paths generally include a plurality of intermediate positions between the initial and ending positions of the teeth. Multiple clear, removable aligners formed to move the teeth to the various positions along the corrective path are then manufactured. One system for providing such aligners is the Invisalign® System from Align Technologies, Inc. of Santa Clara, Calif.

The planning of the corrective paths for the teeth often involves various orthodontic measurements and diagnostics. Many of these measurements utilize a mathematical model of the tooth, including portions of the tooth that are not visible to the naked eye such as its root. Currently, the tooth's axes are constructed manually such that the tooth's model, including its root may be constructed. However, this is a tedious, time consuming process that is subject to human error. Automatic construction of the tooth's axes is desirable as it would save time and eliminate human error.

SUMMARY OF THE INVENTION

Embodiments of the present invention provide apparatus, systems, and methods for automatic construction of a tooth's axes. In accordance with an exemplary embodiment, for a tooth having a ridge such as an incisor, three dimensional data for the tooth is received. A first plane may be calculated that matches the labial area of the tooth and a second plane may be calculated that matches the lingual area of the tooth. A YZ plane may then be calculated for the set of axes, by bisecting the first plane and the second plane. An OZ axis for the set of axes may be calculated, such that the OZ axis approximates an axis of rotation symmetry for the tooth. An OY axis for the set of axes may then be calculated, such that the OY axis is substantially parallel to the ridge of the tooth. A Y coordinate for an origin for the set of axes may be calculated, such that the Y coordinate approximates the mid-point of the ridge of the tooth. Finally, an X coordinate and a Z coordinate for the origin may be calculated, such that the X and Z coordinates are located proximate to a front edge of the tooth.

BRIEF DESCRIPTION OF THE DRAWINGS

A more complete understanding of the present invention may be derived by referring to the detailed description and claims when considered in connection with the drawing Figures, where like reference numbers refer to similar elements throughout the Figures, and:

DETAILED DESCRIPTION OF THE INVENTION

The present invention may be described herein in terms of various components and processing steps. It should be appreciated that such components and steps may be realized by any number of hardware and software components configured to perform the specified functions. For example, the present invention may employ various electronic control devices, visual display devices, input terminals and the like, which may carry out a variety of functions under the control of one or more control systems, microprocessors or other control devices. In addition, the present invention may be practiced in any number of orthodontic contexts and the exemplary embodiments relating to a system and method for automatic detection of dental features are merely a few of the exemplary applications for the invention. For example, the principles, features and methods discussed may be applied to any orthodontic treatment application.

U.S. Pat. Nos. 7,063,532 and 6,514,074, assigned to the same assignee as this application, describe techniques for generating 3-dimensional digital data sets containing models of individual components of a patient's dentition. These data sets include digital models of individual teeth and the gingival tissue surrounding the teeth. Furthermore, these applications also describe computer-implemented techniques for using the digital models in designing and simulating an orthodontic treatment plan for the patient. For example, one such technique involves receiving an initial data set that represents the patient's teeth before treatment, specifying a desired arrangement of the patient's teeth after treatment, and calculating transformations that will move the teeth from the initial to the final positions over desired treatment paths. One technique for producing an orthodontic appliance involves creating a positive mold of the patient's dentition at one of the treatment stages and using a conventional pressure molding technique to form the appliance around the positive mold. A design of orthodontic appliances from the digital dentition models is, for example, described in U.S. patent application Ser. No. 09/169,034, which has issued as U.S. Pat. No. 6,471,511 and is assigned to the same assignee as this application.

Figure 1A:
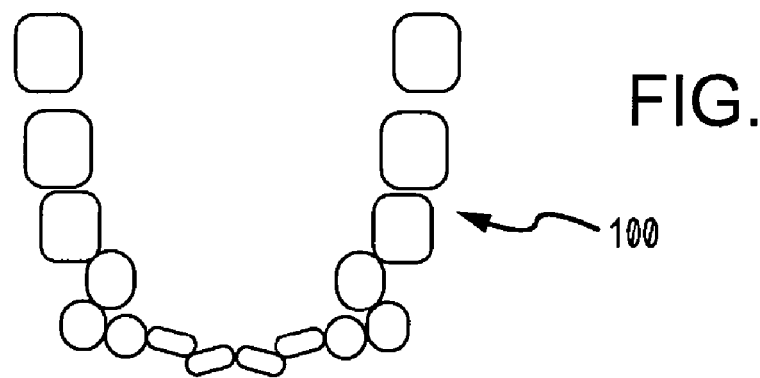
FIGS. 1A, 1B, and 1C are diagrams showing the arrangement of a patient's teeth at an initial stage, an intermediate stage, and a final stage, respectively, of orthodontic treatment.
Figure 1B:
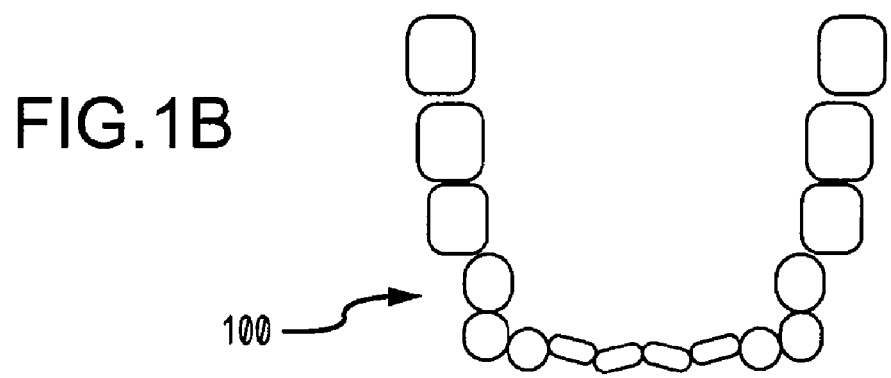
Figure 1C:
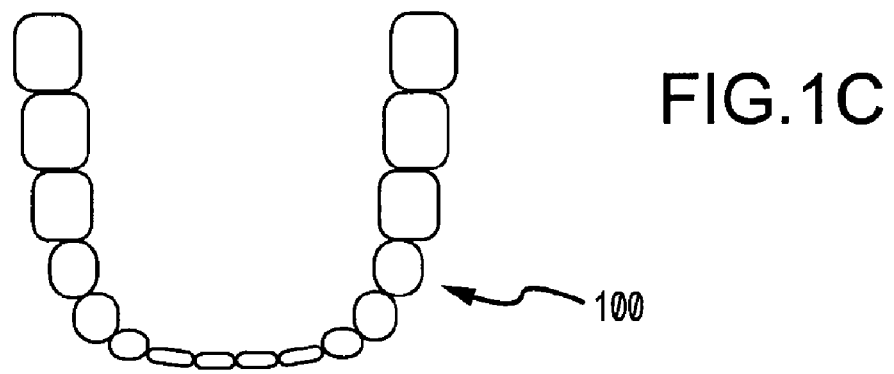

FIGS. 1A, 1B, and 1C show a patient's dentition at three stages during a course of treatment. FIG. 1A illustrates the initial positions of the patient's teeth before treatment begins. A digital model of the teeth at these initial positions is captured in an initial digital data set (IDDS).

Such an IDDS may be obtained in a variety of ways. For example, the patient's teeth may be scanned or imaged using well known technology, such as X-rays, three-dimensional x-rays, computer-aided tomographic images or data sets, magnetic resonance images, and the like.

Methods for digitizing such conventional images to produce data sets are well known and described in the patent and medical literature. By way of example, one approach is to first obtain a plaster cast of the patient's teeth by well known techniques, such as those described in Graber, Orthodontics: Principle and Practice, Second Edition, Saunders, Philadelphia, 1969, pp. 401-415. After the tooth casting is obtained, it can be digitally scanned using a conventional laser scanner or other range acquisition system to produce the IDDS. The data set produced by the range acquisition system may, of course, be converted to other formats to be compatible with the software which is used for manipulating images within the data set. General techniques for producing plaster casts of teeth and generating digital models using laser scanning techniques are described, for example, in U.S. Pat. No. 5,605,459. In accordance with another exemplary embodiment, the acquiring of a digital model of a patient's teeth can also comprise such techniques as disclosed in U.S. Pat. No. 6,767,208, entitled "System and Method for Positioning Teeth", assigned to the same assignee as this application. Accordingly, any methodology or process for converting scanned data into a digital representation or otherwise for the acquiring of a digital model of a patient's teeth can be utilized.

FIG. 1B illustrates an example of how the patient's teeth may be oriented at an intermediate stage in the treatment process, and FIG. 1C illustrates an example of how the patient's teeth may be oriented at their final positions. A human operator and/or a computer program manipulate the digital models of the patient's teeth to prescribe the final tooth positions. The program then calculates one or more of the intermediate positions, taking into account any constraints imposed on the movement of the teeth by the human operator or by the natural characteristics of the teeth themselves. The program also accounts for any collisions that might occur between teeth as the teeth move from one treatment stage to the next. Selecting the final and intermediate tooth positions and the treatment paths along which the teeth move is described in more detail in one or more of the Patent Applications discussed above, which are all hereby incorporated by reference, in their respective entireties.

Figure 1D:
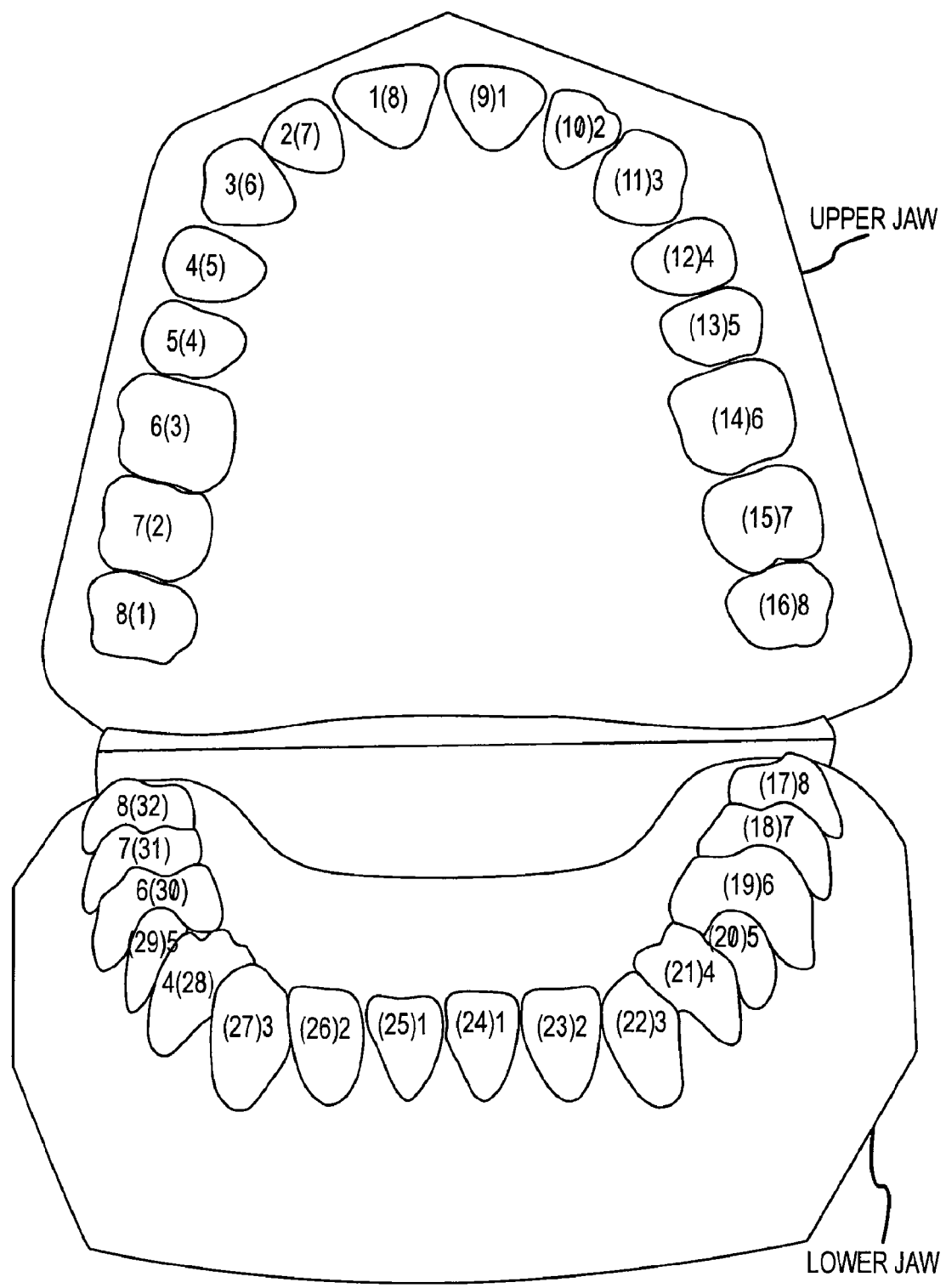
FIG. 1D is a diagram showing teeth numbering according to the standard system of tooth numbering.

FIG. 1D is a diagram of a set of teeth showing the standard system of numbering teeth. Reference is made to this standard system of numbering throughout the discussion below.

Figure 2:
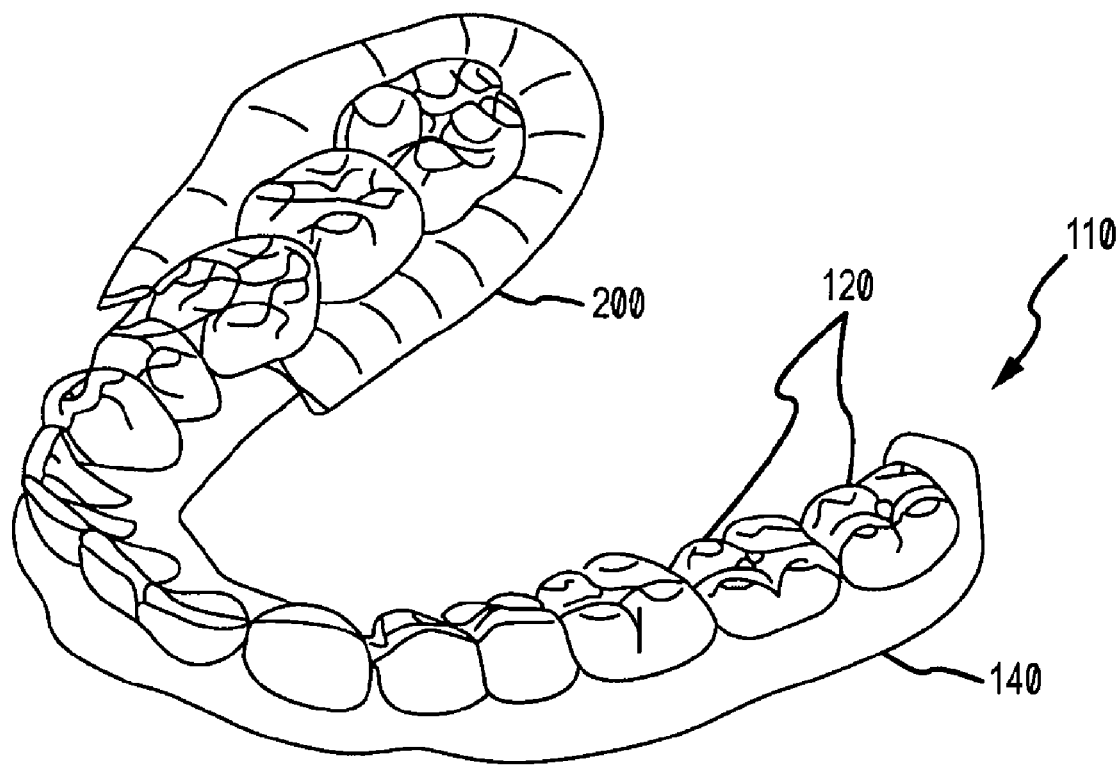
FIG. 2 is a diagram illustrating a partial model of a patient's dentition, including a model of gingival tissue.

FIG. 2 is a diagram illustrating a portion of a typical digital dentition model 110 derived from the IDDS. Dentition model 110 includes models of individual teeth 120 and a model of the patient's gums 140. Various techniques for creating models of gum tissue and individual teeth from the IDDS are described in, for example, U.S. Pat. Nos. 6,409,504 and 7,063,532, both of which are assigned to the same assignee as this application.

Furthermore, FIG. 2 shows a portion of another gingival model 200 (a "secondary" gingival model), which is constructed to overlie gingival model 140 derived from the IDDS (the "primary" gingival model). The program uses the secondary gingival model 200 to model the deformation of the gingival tissue around the patient's teeth as the teeth move from their initial positions to their final positions. This ensures that orthodontic appliances made from positive molds of the patient's dentition fit comfortably around the patient's gums at all treatment stages. The secondary gingival model 200 also adds thickness to the gum model, which ensures that the orthodontic appliances do not press too tightly against the patient's gums.

Reference will now be made to various exemplary embodiments of the invention, which are illustrated in the accompanying figures. While these exemplary embodiments are described in sufficient detail to enable those skilled in the art to practice the invention, it should be understood that other embodiments may be realized and that logical and/or mechanical changes may be made without departing from the spirit and scope of the invention. Thus, the various embodiments herein are presented for purposes of illustration and not by way of limitation. For example, the steps recited in any of the method or process descriptions may be executed in any order and are not limited to the order presented. Moreover, any of the functions or steps may be outsourced to or performed by one or more third parties.

For the sake of brevity, conventional data networking, application development, and other functional aspects of the systems (and components of the individual operating components of the systems) may not be described in detail herein. Furthermore, the connecting lines shown in the various figures contained herein are intended to represent exemplary functional relationships and/or physical connections between the various elements. It should be noted that many alternative and/or additional functional relationships or physical connections may be present in a practical system.

Various embodiments of the present invention include one or more computing devices having programs stored therein for staging the movement of a patient's teeth. The computing device(s) or various components of any computing device discussed herein may include one or more of the following: a host server or other computing systems including a processor for processing digital data; a memory coupled to the processor for storing digital data; an input digitizer coupled to the processor for inputting digital data; an application program stored in the memory and accessible by the processor for directing processing of digital data by the processor; a display device coupled to the processor and memory for displaying information derived from digital data processed by the processor; and a plurality of databases. Various file indexes and/or databases used herein may include: client data; merchant data; and/or other similar useful data.

As those skilled in the art will appreciate, any computing device utilized by a user may include an operating system (e.g., Windows NT, 95/98/2000, OS2, UNIX, Linux, Solaris, MacOS, etc.) as well as various conventional support software and drivers typically associated with computers. As will be appreciated by one of ordinary skill in the art, each computing device may be embodied as a customization of an existing system, an add-on product, upgraded software, a stand alone system, a distributed system, a method, a data processing system, a device for data processing, and/or a computer program product. Accordingly, any program stored therein may take the form of an entirely software embodiment, an entirely hardware embodiment, or an embodiment combining aspects of both software and hardware. Furthermore, any program may take the form of a computer program product on a computer-readable storage medium having computer-readable program code means embodied in the storage medium. Any suitable computer-readable storage medium may be utilized, including hard disks, CD-ROM, optical storage devices, magnetic storage devices, and/or the like.

In accordance with one exemplary embodiment, a computing device is configured to receive an electronic representation of the patient's teeth in an initial position taken by, for example, an intra-oral scanner or a CT scanner based on an impression or partial impression of the patient's teeth. The received data includes three dimensional data for the patient's teeth that can be used as input into the various embodiments of the present invention for automatic detection of the teeth's features. In addition, the computing device is configured to receive or generate an electronic representation of a desired final position for each of the patient's teeth. The program stored within the computing device is configured to analyze the initial and final positions, and automatically create a route for each tooth to move from its initial position to its final position. A set of aligners to move the teeth along the path in various stages is manufactured for the patient. As the patient wears the aligners, the patient's teeth move along the path according to each stage.

In order to analyze the initial, intermediate and final positions of the teeth, various orthodontic measurements and diagnostics are taken that utilize the teeth's model, including portions of the tooth that are not visible to the naked eye such as its root. Automatic construction of the tooth's axes may be performed using the visible part of the crown shape (i.e., clinical crown) and the facial axes of the clinical crown (FACC) curve of the tooth.

Figure 3:
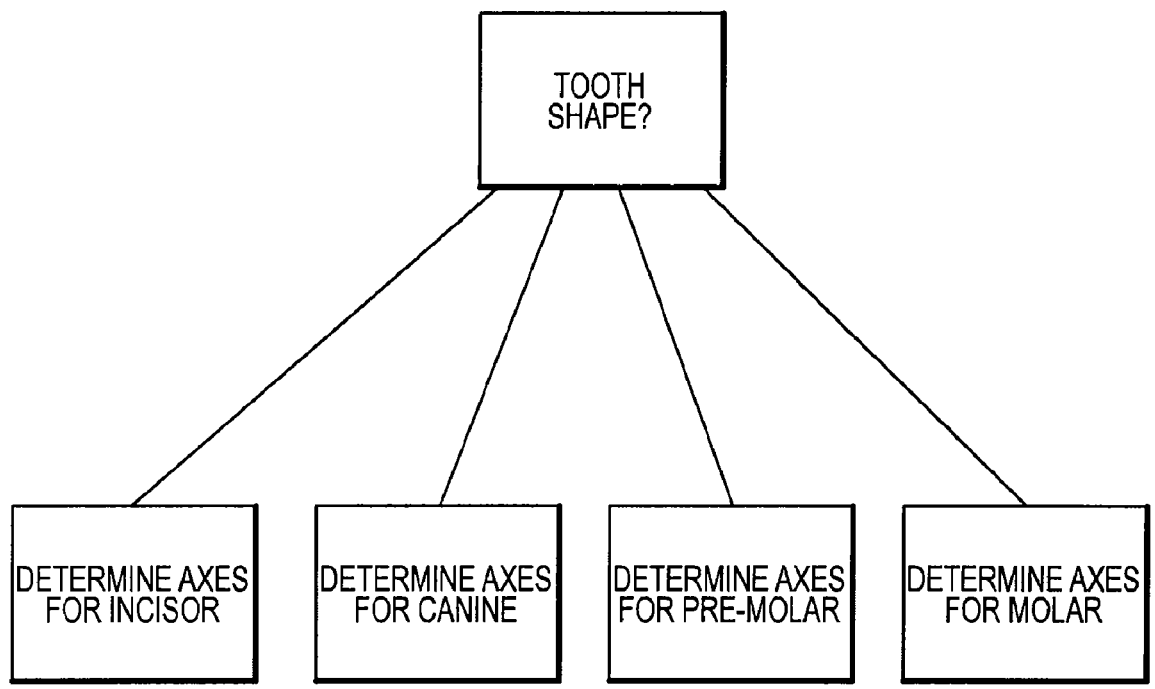
FIG. 3 is a flow diagram of an exemplary method to determine the axes for a particular type of tooth.

With reference to FIG. 3, in accordance with one embodiment of the present invention, the automatic construction of a tooth's axes will utilize the tooth crown shape. That is, the automatic construction of the tooth's axes will vary for different types of teeth such as incisors, canines, premolars, and molars as will be described next.

Incisors

Figure 4:
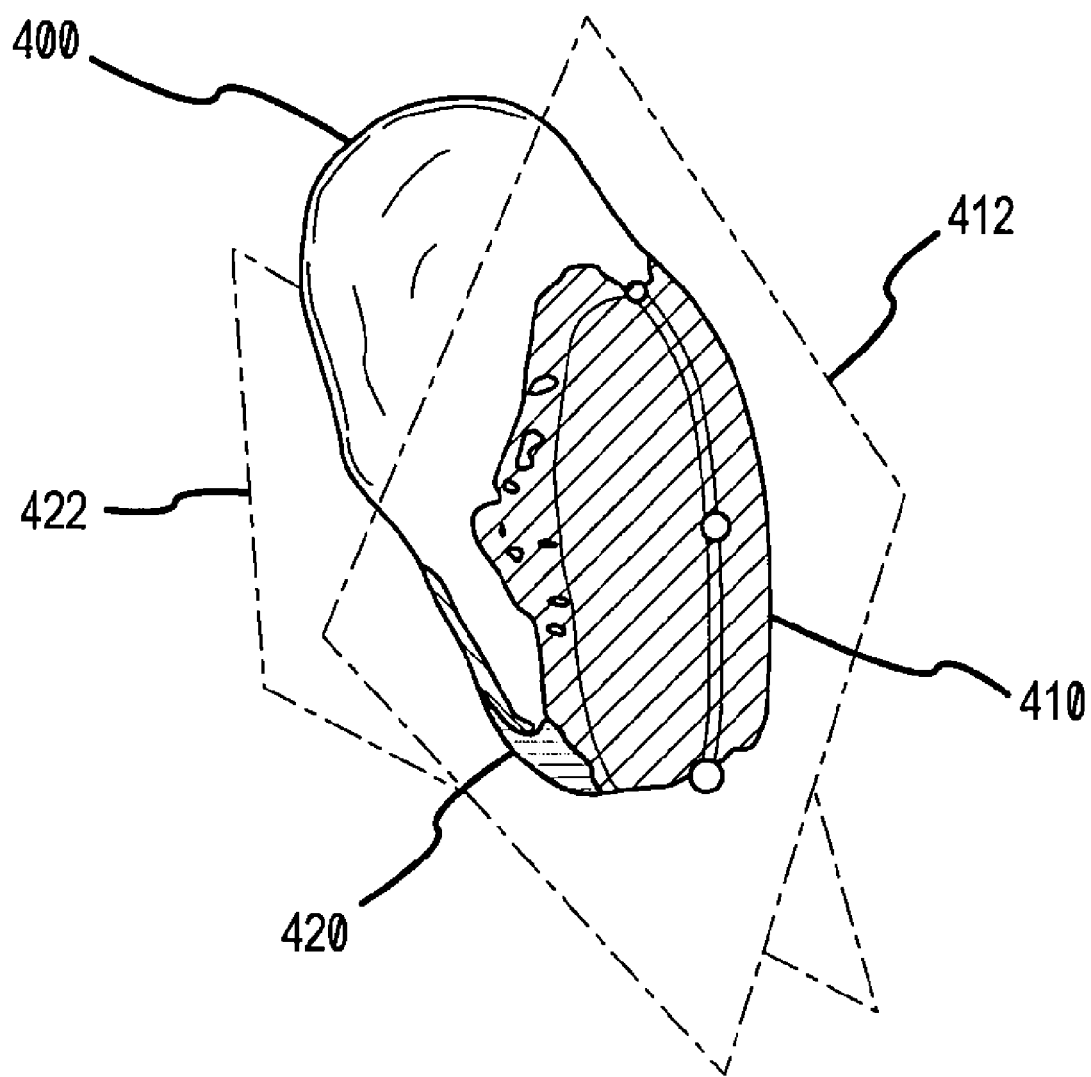
FIG. 4 is a diagram of an exemplary incisor with calculated diagnostics in accordance with an exemplary embodiment of the present invention.
Figure 5:
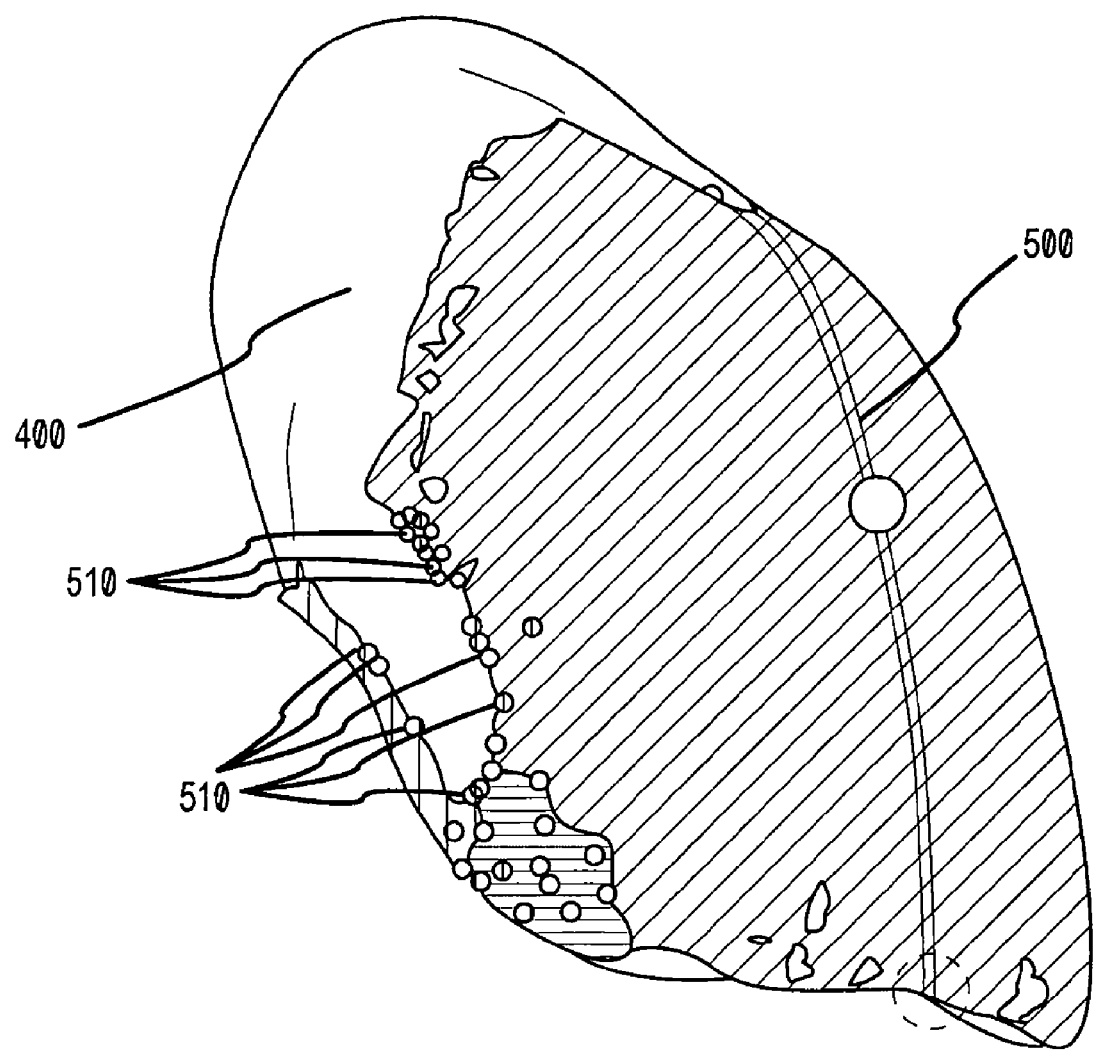
FIG. 5 is a diagram of an exemplary incisor with calculated diagnostics in accordance with an exemplary embodiment of the present invention.

With reference to FIG. 4, an incisor 400 is illustrated having labial 410 and lingual 420 areas. Labial area 410 may be approximated by a plane 412. As mentioned above, input data is received in the form of three dimensional data that represents the initial position of the teeth. In accordance with an exemplary embodiment, plane 412 may be calculated by surveying the three dimensional data for the labial area. Plane 412 is calculated by utilizing a best fit or similar method to best match the set of points for labial area 410. Lingual area 420 may also be approximated by a plane 422. Similar to plane 412, plane 422 may be calculated by surveying the three dimensional data for lingual area 420. Plane 422 is calculated by utilizing a best fit or similar method to best match the set of points for lingual area 420.

In accordance with an exemplary embodiment of the present invention, an orthogonal (i.e., x,y,z) frame of reference is used to specify the axes of a tooth. The YZ plane of the tooth's axes is a plane that is balanced between labial area 410 and lingual area 420. The YZ plane may be calculated by bisecting labial plane 412 and lingual plane 422.

With reference to FIGS. 5, 6 and 17A-C, an OZ axis 500 of incisor 400 is reconstructed as the axis of rotation symmetry of the incisor. Rotation symmetry of the incisor refers to the property where the incisor may be rotated 180 degrees around the axis, and still be roughly equal to its original shape. The axis of rotation symmetry may be estimated by a shape matching algorithm as described next. In accordance with an exemplary embodiment of the present invention, OZ axis 500 may be calculated by utilizing bounding box 630 for the incisor, such that OZ axis 500 is in the middle of the bounding box. Next, with reference to FIGS. 17A-C, incisor 400 may be rotated by 180 degrees around OZ axis 500. Each vertex in the crown is paired to the nearest vertex from the original model (i.e., incisor in its original position) and a rigid-body transformation (i.e., rotation and translation matrix) can be computed from the paired points. A new OZ axis is calculated from the transformation matrix, and these steps may be repeated to minimize errors in the OZ axis.

In accordance with one aspect of the present invention, errors in the reconstruction of the OZ axis may be reduced by comparing it with the axis balanced between the left and right borders (i.e., center of mass) of the tooth's three dimensional mesh. If the calculated OZ axis is more than a configurable amount, such as 10%, from the center of mass, then the operator may be notified to determine whether the calculated OZ axis is in an acceptable position. With continued reference to FIG. 5, border vertices 510 mark the border of incisor's 400 three dimensional tooth mesh.

Figure 6:
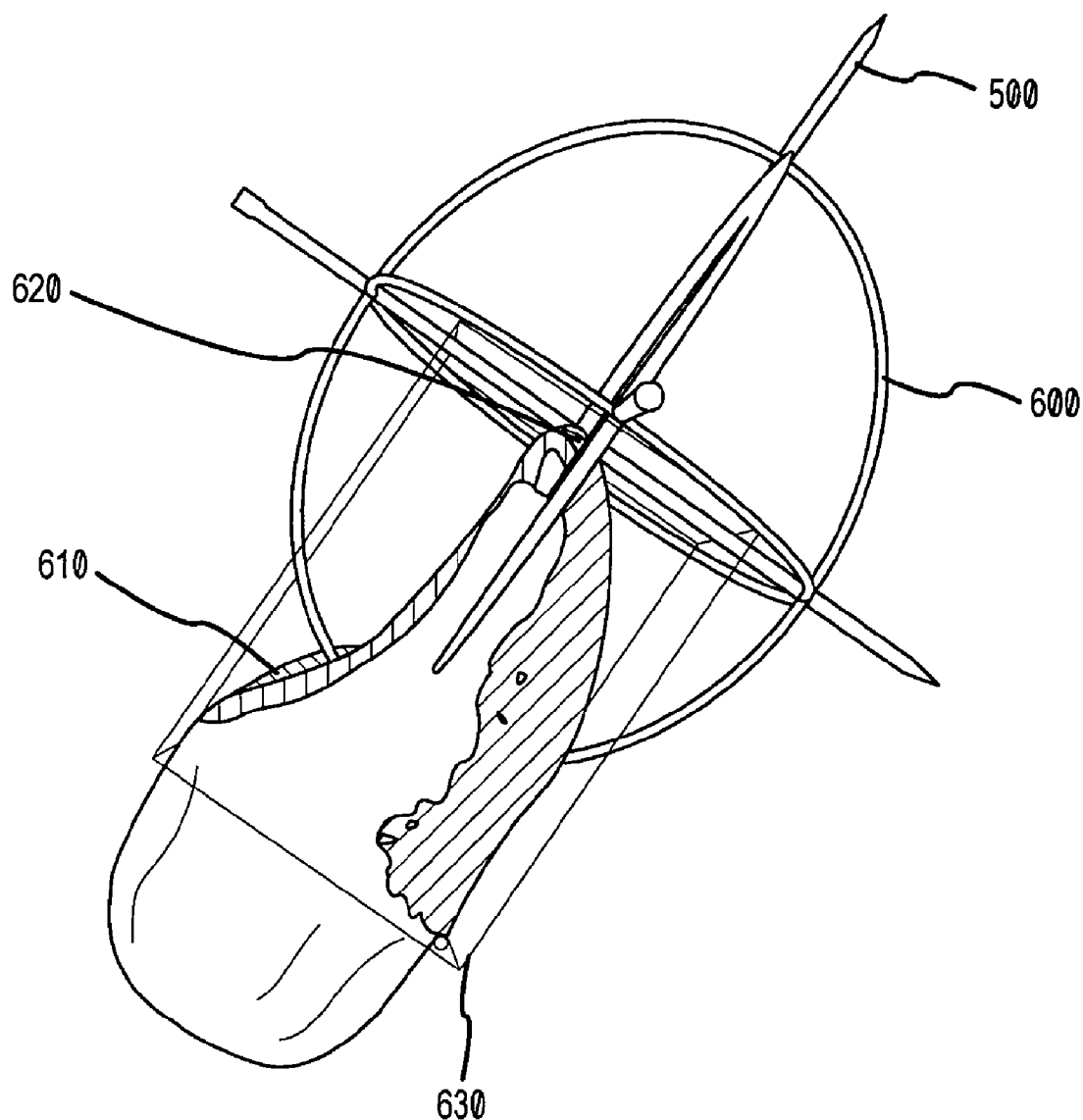
FIG. 6 is a diagram of an exemplary incisor with calculated diagnostics in accordance with an exemplary embodiment of the present invention.

With reference to FIG. 6, an OY axis 600 of the tooth's axes set is constructed such that axis 600 is parallel to ridge 610 of incisor 400. For incisors, ridge 610 is the surface area of the tooth that is used for eating. Origin 620 of the tooth's axes is defined by (x,y,z) coordinates. The Y coordinate of origin 620 is calculated by detecting the mid-point of the tooth's ridge (i.e., the middle of the tooth in the y-direction). In accordance with an exemplary embodiment, the X and Z coordinates of origin 620 are shifted to the front/top edge of incisor 400 such that the axes are in the middle of bounding box 630.

Canines

Figure 7:
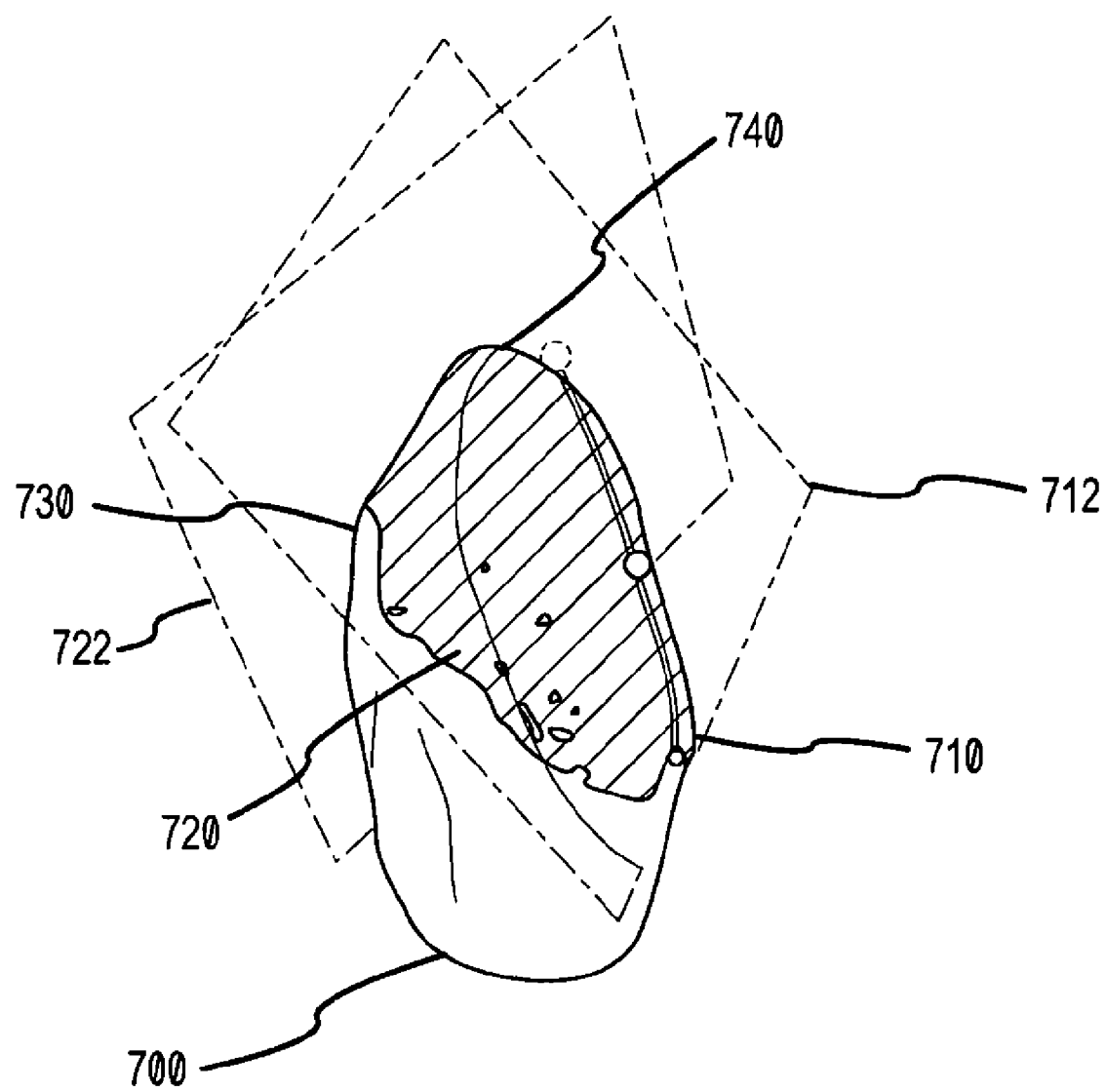
FIG. 7 is a diagram of an exemplary canine with calculated diagnostics in accordance with an exemplary embodiment of the present invention.

With reference to FIG. 7, a canine 700 is illustrated having labial 710 and lingual 720 areas. Labial area 710 may be approximated by a plane 712. As mentioned above, input data is received in the form of three dimensional data that represents the initial position of the teeth. In accordance with an exemplary embodiment, plane 712 may be calculated by surveying the three dimensional data for the labial area. Plane 712 is calculated by utilizing a best fit or similar method to best match the set of points for labial area 710. Lingual area 720 may also be approximated by a plane 722. Similar to plane 712, plane 722 may be calculated by surveying the three dimensional data for lingual area 720. Plane 722 is calculated by utilizing a best fit or similar method to best match the set of points for lingual area 720.

Canine 700 also includes a cusp 740 that is a pointed projection on the tooth. The cusp is a major tooth anatomy feature and is located on the grinding surface of canine 700. Other teeth, such as pre-molars and molars may have more than one cusp.

In accordance with an exemplary embodiment of the present invention, an orthogonal (i.e., x,y,z) frame of reference is used to specify the axes of canine 700. The YZ plane of canine's 700 axes is a plane that is balanced between labial area 710 and lingual area 720. The YZ plane may be calculated by bisecting labial plane 712 and lingual plane 722.

Figure 8:
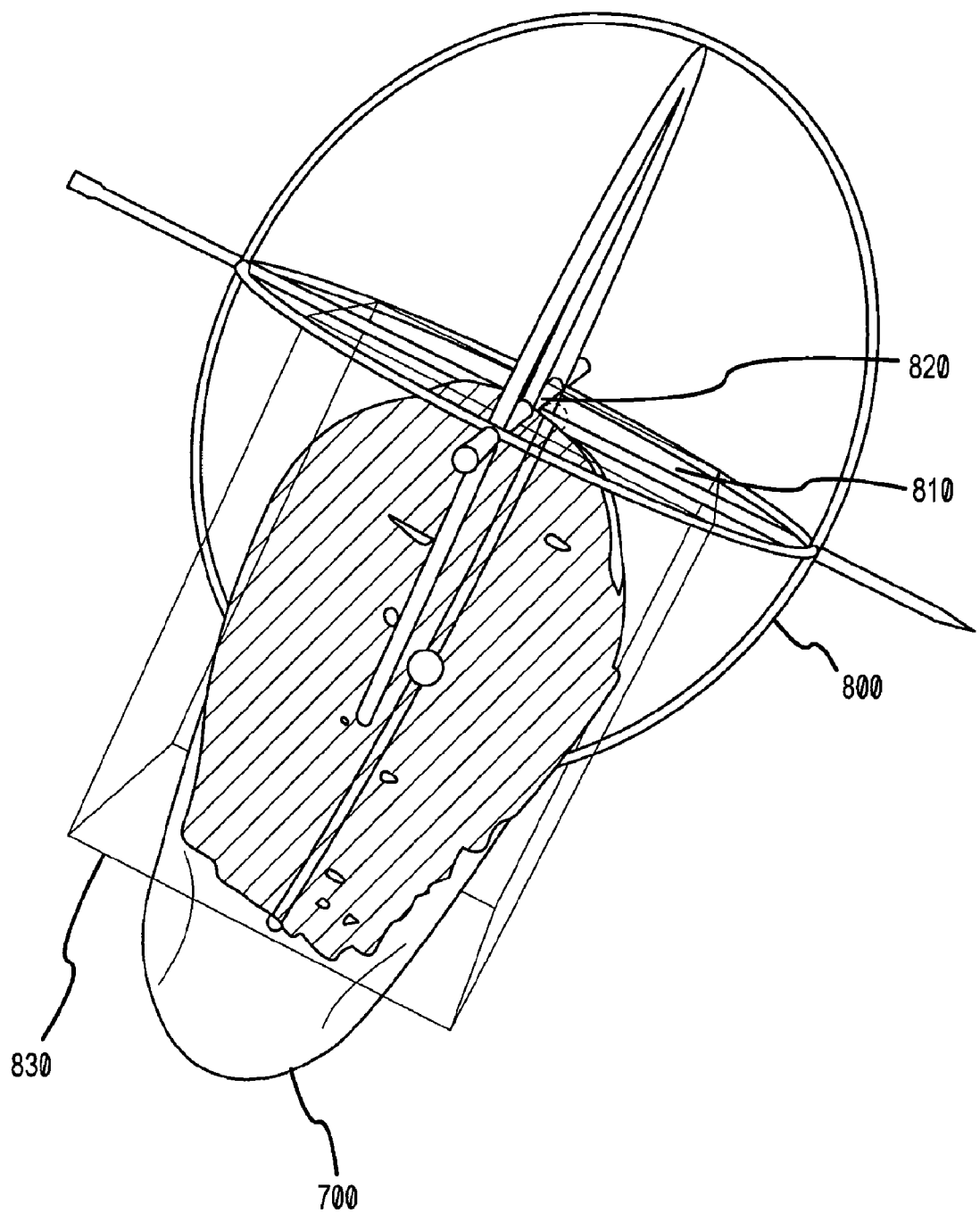
FIG. 8 is a diagram of an exemplary canine with calculated diagnostics in accordance with an exemplary embodiment of FIG. 9 is a diagram of an exemplary premolar with calculated diagnostics in accordance with an exemplary embodiment of the present invention.

With reference to FIGS. 7 and 8, an OZ axis 800 of canine 700 is reconstructed as the axis of rotation symmetry of the tooth. In accordance with an exemplary embodiment of the present invention, OZ axis 800 may be calculated by utilizing bounding box 830 for the canine, such that OZ axis 800 is in the middle of the bounding box. An OY axis 810 of the tooth's axes set is constructed such that axis 810 is parallel to a ridge 730 of canine 700. In accordance with an exemplary embodiment of the present invention, ridge 730 may be defined as the border between labial area 710 and lingual area 720. Origin 820 of the tooth's axes is defined by (x,y,z) coordinates. The Y coordinate of origin 820 is calculated by detecting the mid-point of ridge 730 (i.e., the middle of the tooth in the y-direction). In accordance with an alternative embodiment of the present invention, origin 820 may be set to the tip of cusp 740 of canine 700.

Premolars

Figure 9:
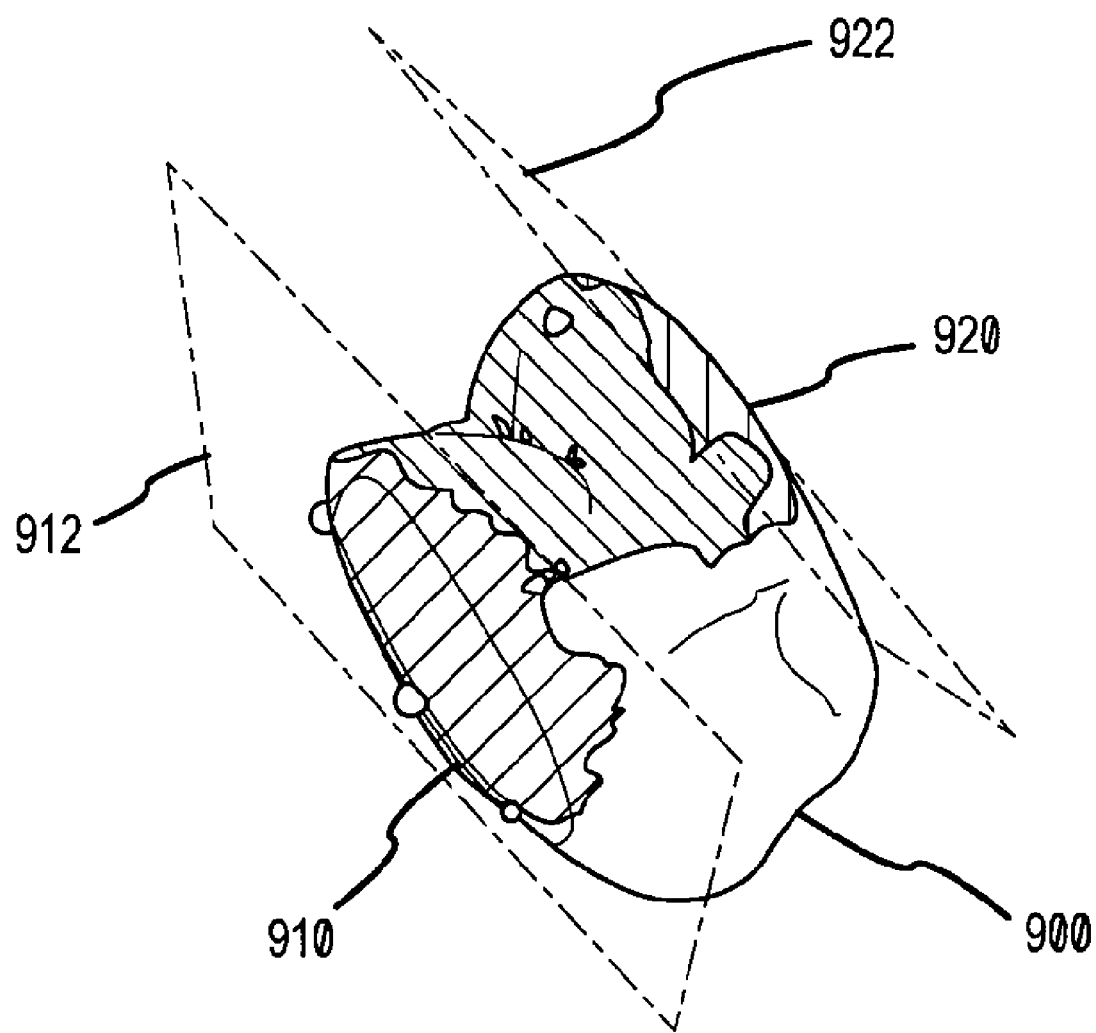

With reference to FIG. 9, a premolar 900 is illustrated having labial area 910, lingual area 920, cusps 930, and crown 940. The crown of a tooth is generally defined as the portion of the tooth that is covered by enamel. Labial area 910 may be approximated by a plane 912. As mentioned above, input data is received in the form of three dimensional data that represents the initial position of the teeth. In accordance with an exemplary embodiment, plane 912 may be calculated by surveying the three dimensional data for the labial area. Plane 912 is calculated by utilizing a best fit or similar method to best match the set of points for labial area 910. Lingual area 920 may also be approximated by a plane 922. Similar to plane 912, plane 922 may be calculated by surveying the three dimensional data for lingual area 920. Plane 922 is calculated by utilizing a best fit or similar method to best match the set of points for lingual area 920.

In accordance with an exemplary embodiment of the present invention, an orthogonal (i.e., x,y,z) frame of reference is used to specify the axes of premolar 900. The YZ plane of premolar's 900 axes is a plane that is balanced between labial area 910 and lingual area 920. The YZ plane may be calculated by bisecting labial plane 912 and lingual plane 922.

Figure 10:
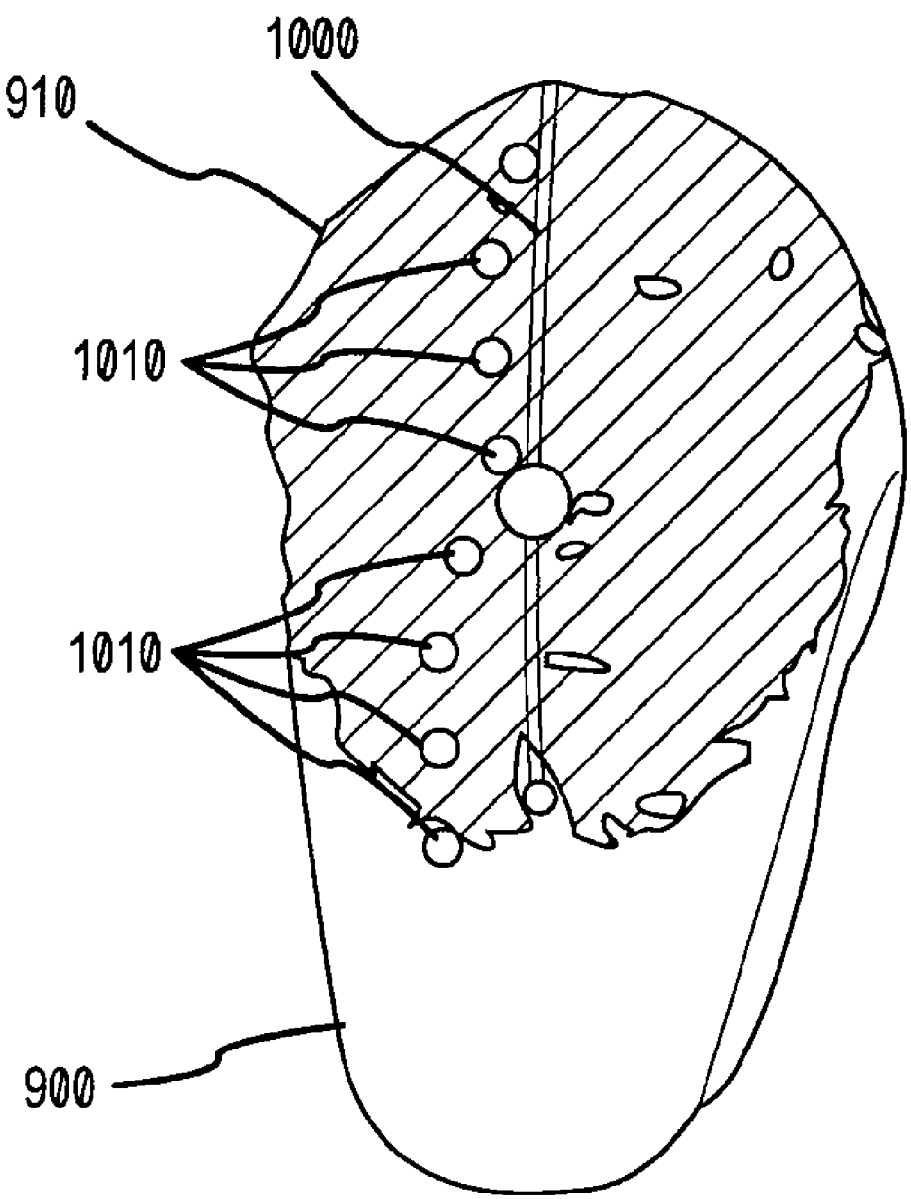
FIG. 10 is a diagram of an exemplary premolar with calculated diagnostics in accordance with an exemplary embodiment of the present invention.

With reference to FIG. 10, an OZ axis 1000 of premolar 900 is reconstructed so that it is parallel to a line approximated by points 1010 from the labial area 910. In accordance with an exemplary embodiment of the present invention, points 1010 may be selected from labial surface 920, such that points 1010 are distal from the calculated YZ plane of premolar's 900 tooth axes. In accordance with one embodiment of the present invention, the selected points may be the most prominent points of the labial surface.

Figure 11:
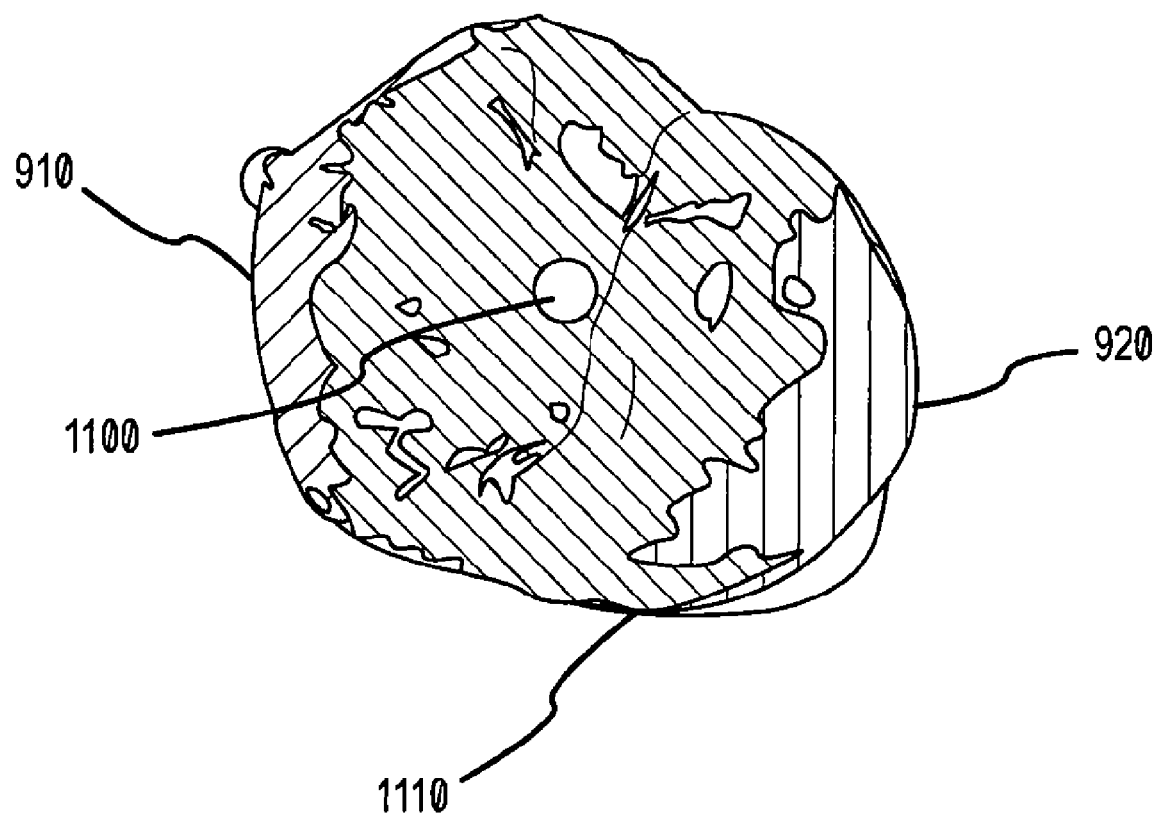
FIG. 11 is a diagram of an exemplary premolar with calculated diagnostics in accordance with an exemplary embodiment of the present invention.
Figure 12:
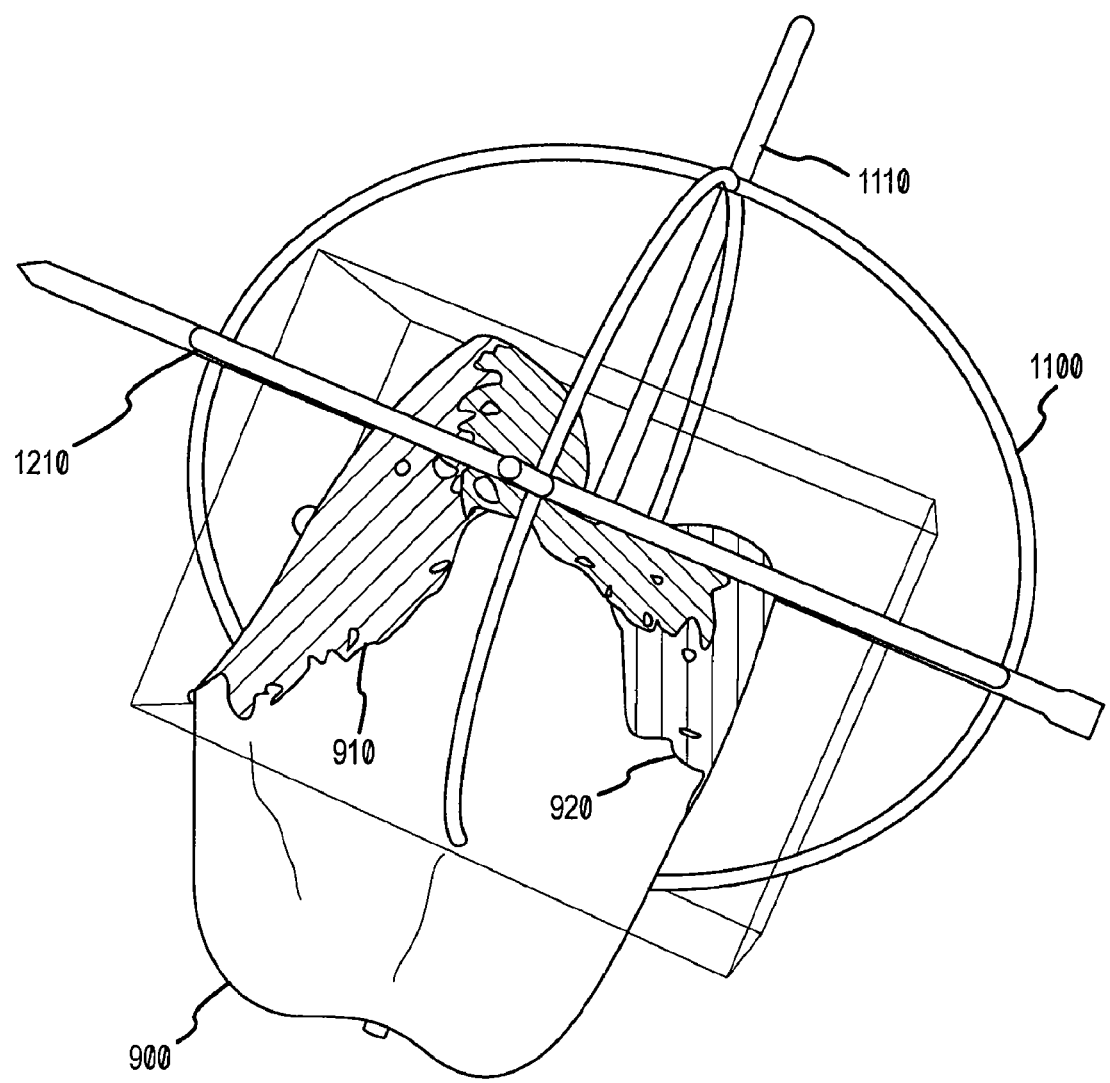
FIG. 12 is a diagram of an exemplary premolar with calculated diagnostics in accordance with an exemplary embodiment of the present invention.

With reference to FIG. 11, origin 1100 of the premolar's tooth axes is located in the center of the tooth on crown 940. With reference to FIG. 12, an OX axis 1210 of the tooth's axes set is constructed such that axis 1210 is parallel to a line going through cusps 930 of premolar 900.

Molars

Figure 13:
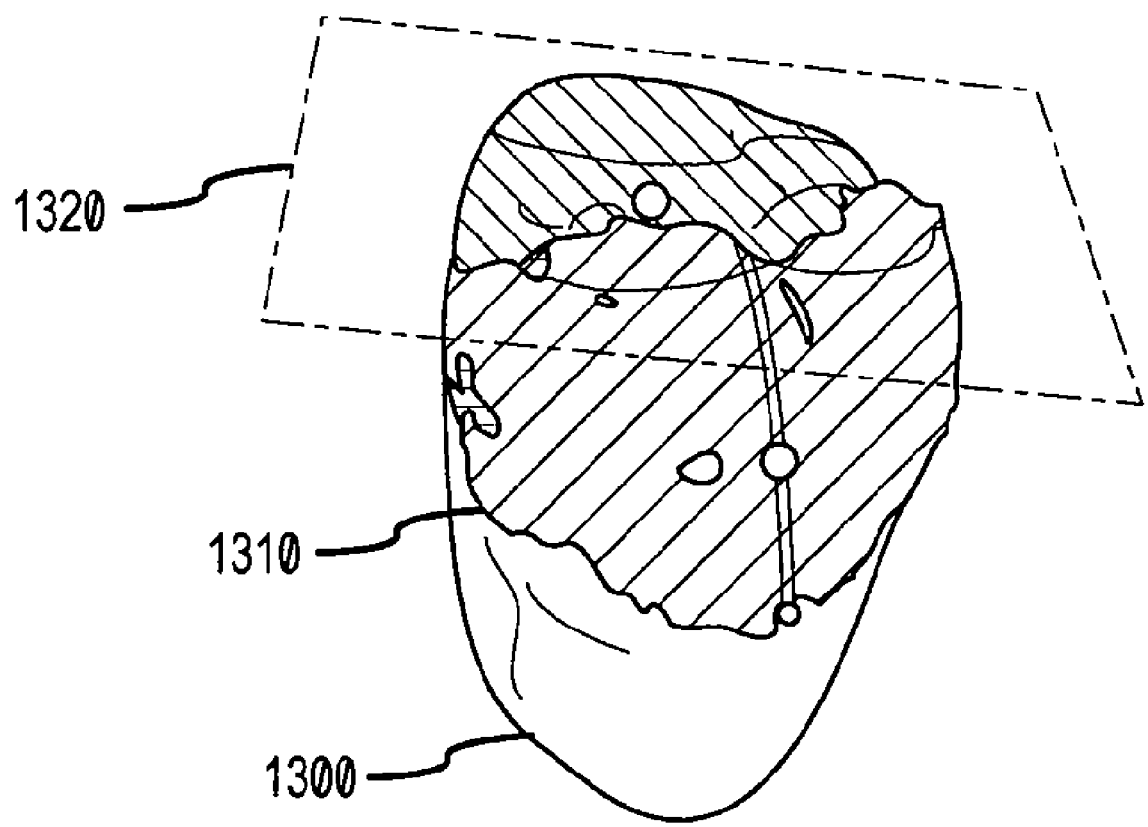
FIG. 13 is a diagram of an exemplary molar with calculated diagnostics in accordance with an exemplary embodiment of the present invention.

With reference to FIG. 13, molar 1300 is illustrated having four cusps 1330 and crown 1340. In accordance with an exemplary embodiment of the present invention, occlusal surface 1310 may be approximated by a plane that best fits the cusps. The plane may be calculated utilizing a means square approach (i.e., "least squares approach") or similar method. An OZ axis of molar 1300 tooth axes may be calculated such that the axis is orthogonal to occlusal surface 1310.

Figure 14:
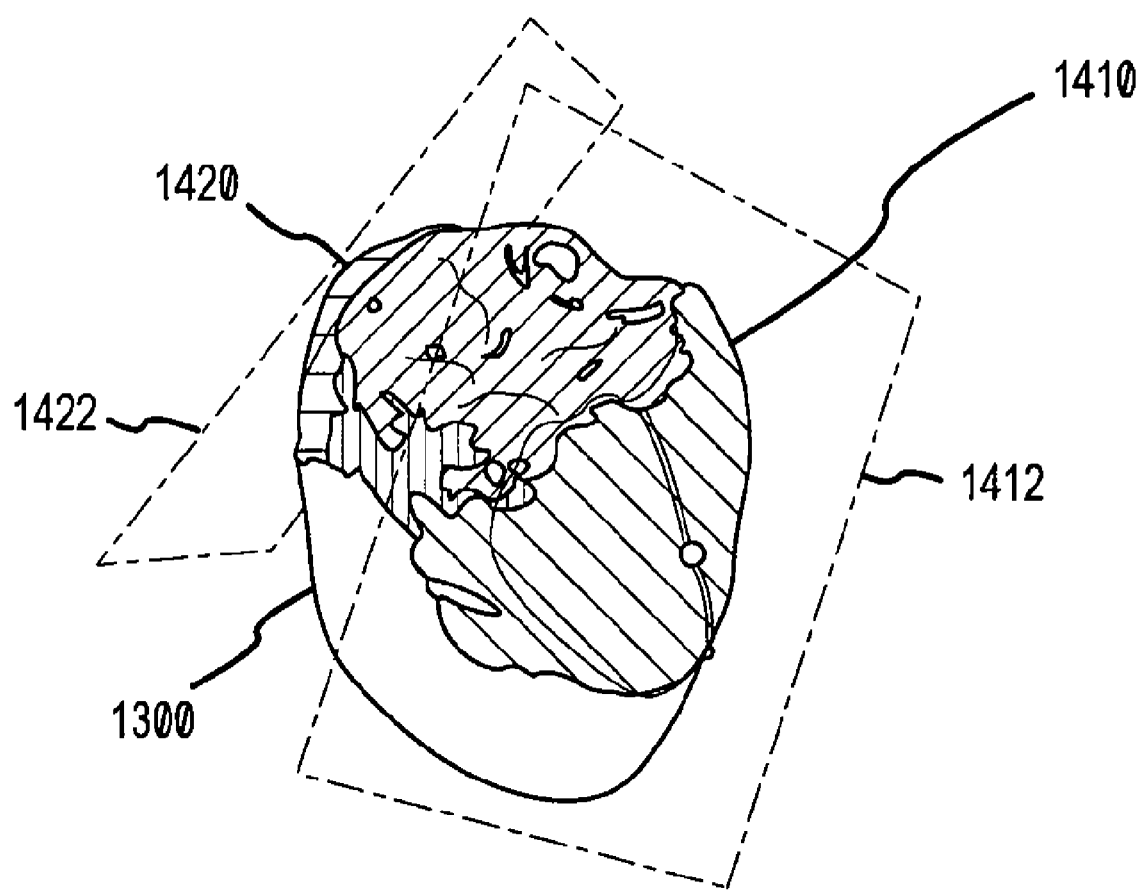
FIG. 14 is a diagram of an exemplary molar with calculated diagnostics in accordance with an exemplary embodiment of the present invention.

With reference to FIG. 14, molar 1300 is illustrated having labial 1410 and lingual 1420 areas. Labial area 1410 may be approximated by a plane 1412.

As mentioned above, input data is received in the form of three dimensional data that represents the initial position of the teeth. In accordance with an exemplary embodiment, plane 1412 may be calculated by surveying the three dimensional data for the labial area. Plane 1412 is calculated by utilizing a best fit or similar method to best match the set of points for labial area 1410. Lingual area 1420 may also be approximated by a plane 1422. Similar to plane 1412, plane 1422 may be calculated by surveying the three dimensional data for lingual area 1420. Plane 1422 is calculated by utilizing a best fit or similar method to best match the set of points for lingual area 1420.

The YZ plane of molar's 1300 axes is a plane that is balanced between labial area 1410 and lingual area 1420. The YZ plane may be calculated by bisecting labial plane 1412 and lingual plane 1422.

Figure 15:
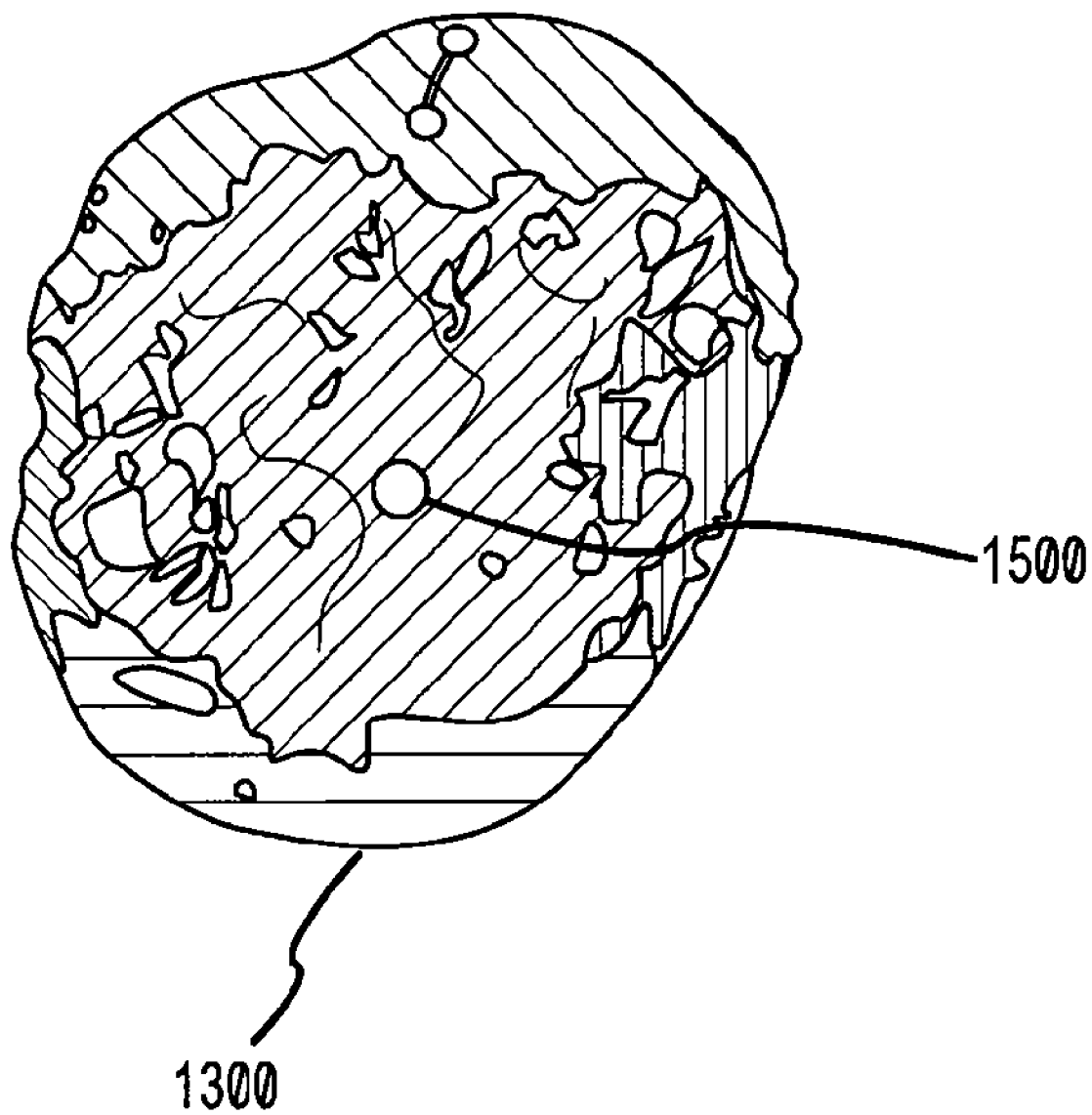
FIG. 15 is a diagram of an exemplary molar with calculated diagnostics in accordance with an exemplary embodiment of the present invention.
Figure 16:
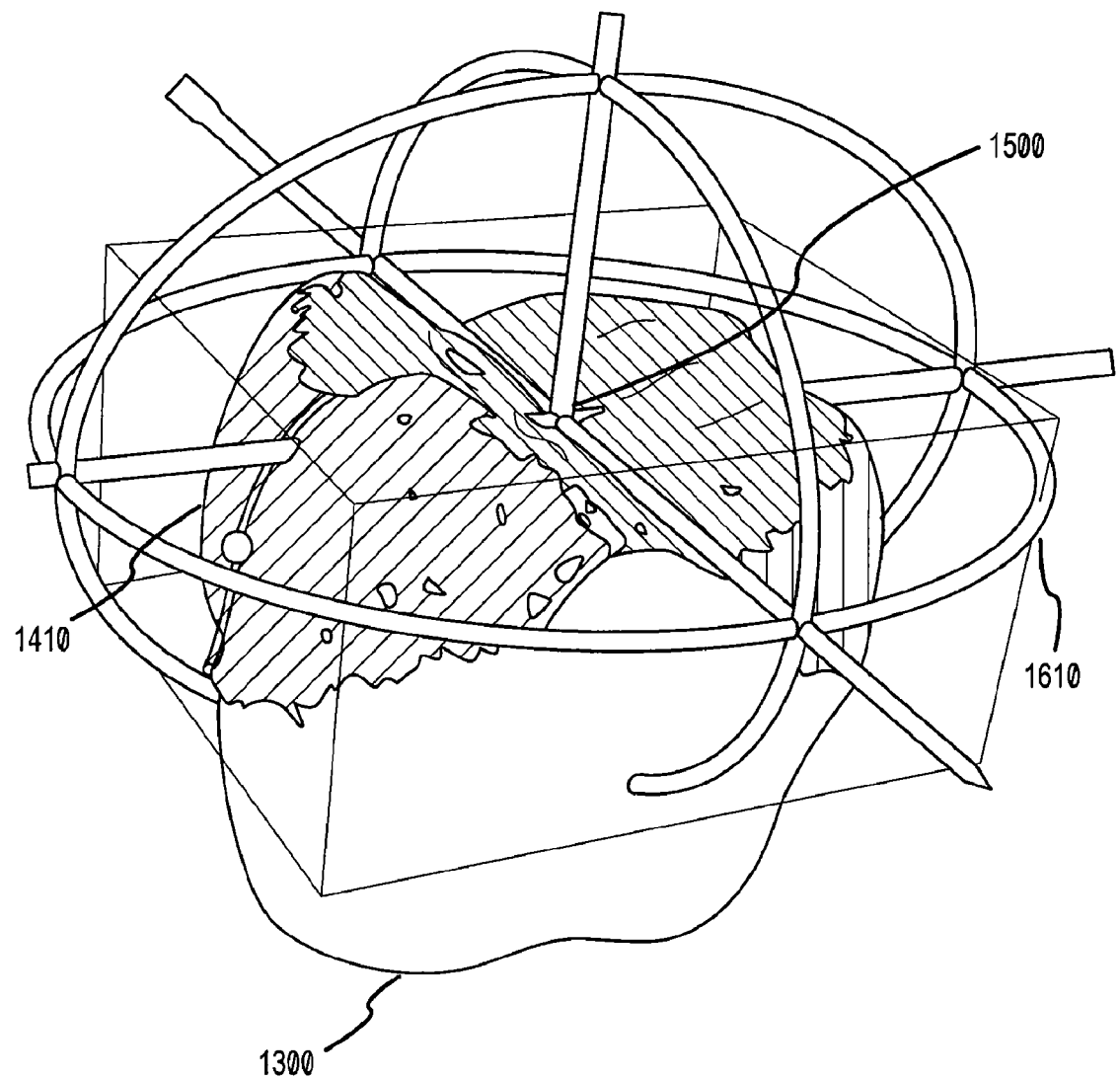
FIG. 16 is a diagram of an exemplary molar with calculated diagnostics in accordance with an exemplary embodiment of the present invention.
Figure 17C:
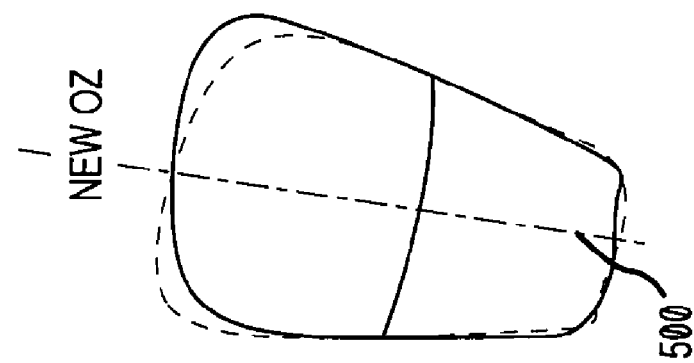
FIGS. 17A-C illustrate an exemplary incisor with calculated diagnostics in accordance with an exemplary embodiment of the present invention.
Figure 17B:
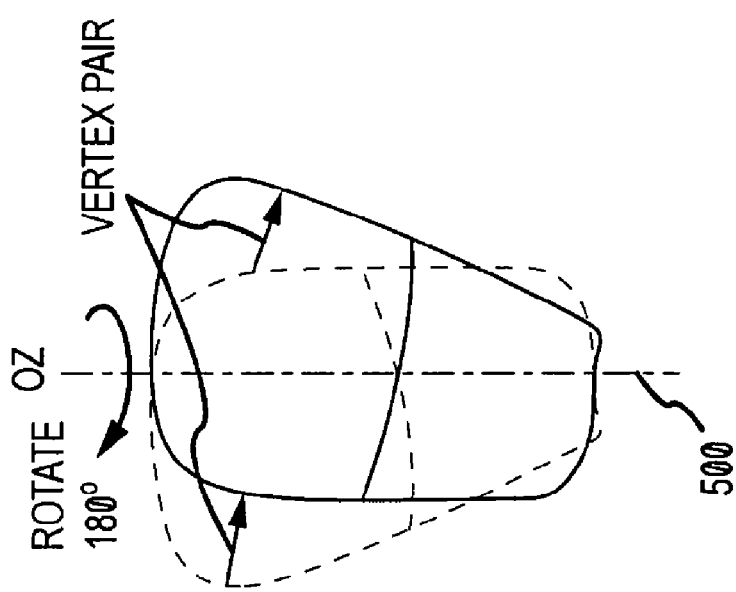
Figure 17A:
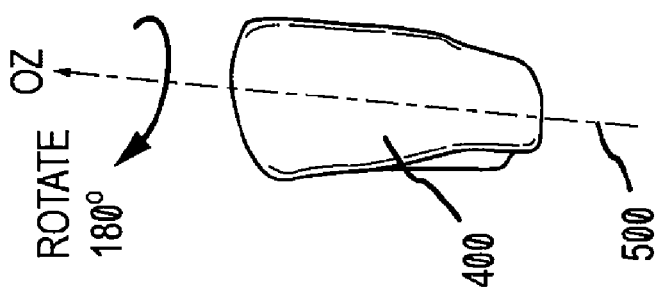

With reference to FIGS. 15 and 16, origin 1500 of the molar's tooth axes is located in the center of the tooth on crown 1340. An OX axis 1610 of the tooth's axes set is constructed such that axis 1610 is parallel to a line that bisects cusps 1330 in the x direction.

Benefits, other advantages, and solutions to problems have been described herein with regard to specific embodiments. However, the benefits, advantages, solutions to problems, and any element(s) that may cause any benefit, advantage, or solution to occur or become more pronounced are not to be construed as critical, required, or essential features or elements of any or all the claims or the invention. The scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described exemplary embodiments that are known to those of ordinary skill in the art are expressly incorporated herein by reference and are intended to be encompassed by the present claims.

We claim:

1. A computer-implemented method for automatic construction of a set of axes for an incisor, comprising:
   receiving three dimensional data for the incisor by the computer;
   calculating an OZ axis for the incisor by calculating an axis that bisects a three dimensional bounding box for the incisor, such that the OZ axis approximates an axis of rotation symmetry for the incisor by the computer without operator intervention, wherein calculating the OZ axis further comprises:
   rotating the incisor about the OZ axis by 180 degrees;
   pairing a number of vertices in the incisor with a respective number of nearest vertices in the unrotated incisor;
   calculating a rigid body transformation from the number of paired vertices; and
   calculating a new OZ axis from the transformation; and
   calculating, an OY axis for the incisor, such that the OY axis is substantially parallel to the ridge of the incisor by the computer without operator intervention.

2. The computer-implemented method of claim 1, further comprising:
   calculating a first plane that approximates a labial area of the incisor;
   calculating a second plane that approximates a lingual area of the incisor;
   calculating a YZ plane, for the set of axes, wherein the YZ plane is approximately balanced between the labial area and the lingual area of the incisor;
   calculating a Y coordinate for an origin for the set of axes, such that the Y coordinate approximates a mid-point of the ridge of the incisor; and
   calculating an X coordinate and a Z coordinate for the origin, such that the X and Z coordinates are located proximate to a front edge of the incisor.

3. The computer-implemented method of claim 2, wherein the step of calculating a YZ, plane comprises calculating a plane that is approximately balanced between the first plane for the labial area of the incisor and the second plane for the lingual area of the incisor.

4. The computer-implemented method of claim 2, wherein:
   the step of calculating a first plane further comprises utilizing a best fit to match a set of three dimensional points for the labial area of the incisor; and
   the step of calculating a second plane further comprises utilizing a best fit to match a set of three dimensional points for the lingual area of the incisor.

5. The computer-implemented method of claim 1, wherein the step of calculating an OZ axis further comprises repeating the rotating, pairing, and calculating steps to reduce errors in the OZ axis.

6. The computer-implemented method of claim 5, wherein the step of calculating an OZ axis further comprises:
   calculating a second OZ axis balanced between left and right borders of a three dimensional mesh of the incisor;
   determining if the OZ axis is more than a configurable amount different than the second OZ axis; and
   notifying the operator to determine whether the OZ axis is in an acceptable position.

7. A computer-implemented method for automatic construction of a set of axes for a tooth having a pair of cusps and a crown, comprising:
   receiving three dimensional data for the tooth by the computer;
   calculating a first plane that approximates a labial area of the tooth by the computer without operator intervention;
   calculating a second plane that approximates a lingual area of the tooth by the computer without operator intervention;
   calculating a YZ plane, for the set of axes, wherein the YZ plane is approximately balanced between the labial area and the lingual area of the tooth by the computer without operator intervention; and
   calculating an OZ axis for the tooth by the computer without operator intervention, such that the OZ axis approximates an axis matching a number of pre-selected points most distal from the YZ plane on the labial area of the tooth.

8. The computer-implemented method of claim 7, further comprising:
   calculating an origin for the set of axes, such that the origin approximates the center of the crown of the tooth.

9. The computer-implemented method of claim 8, wherein:
   the step of calculating a first plane further comprises utilizing a best fit to match a set of three dimensional points for the labial area of the tooth; and
   the step of calculating a second plane further comprises utilizing a best fit to match a set of three dimensional points for the lingual area of the tooth.

10. The computer-implemented method of claim 8, wherein the step of calculating a YZ plane comprises bisecting the first plane that approximates the labial area of the tooth and the second plane that approximates the lingual area of the tooth.

11. A computerized system for automatic construction of a set of axes for an incisor, the computerized system comprising:
   a microprocessor;
   a memory device; and
   wherein the computerized system is configured for:
   receiving three dimensional data for the incisor;
   calculating a first plane that approximates a labial area of the incisor;
   calculating a second plane that approximates a lingual area of the incisor;

calculating a YZ plane, for the set of axes, that is approximately balanced between the first plane for the labial area of the incisor and the second plane for the lingual area of the incisor;

calculating an OZ axis for the set of axes, such that the OZ axis approximates an axis of rotation symmetry for the incisor by calculating an axis that bisects a three dimensional bounding box for the incisor, wherein calculating the OZ axis further comprises:

rotating the incisor about the OZ axis by 180 degrees;

pairing a number of vertices in the tooth with a respective number of nearest vertices in the unrotated tooth;

calculating a rigid body transformation from the number of paired vertices; and calculating a new OZ axis from the transformation:

calculating an OY axis for the set of axes, such that the OY axis is substantially parallel to the ridge of the incisor;

calculating a Y coordinate for an origin for the set of axes, such that the Y coordinate approximates the cusp of the incisor; and calculating an X coordinate and a Z coordinate for the origin, such that the X and Z coordinates are located proximate to a front edge of the incisor.

* * * * *